(12) United States Patent
Paulasaari

(10) Patent No.: US 9,458,183 B2
(45) Date of Patent: Oct. 4, 2016

(54) METHOD OF SYNTHESIZING SILOXANE MONOMERS AND USE THEREOF

(75) Inventor: Jyri Paulasaari, Espoo (FI)

(73) Assignee: Silecs Oy, Espoo (FI)

( * ) Notice: Subject to any disclaimer, the term of this patent is extended or adjusted under 35 U.S.C. 154(b) by 0 days.

(21) Appl. No.: 14/126,446

(22) PCT Filed: Jun. 14, 2012

(86) PCT No.: PCT/FI2012/050601
§ 371 (c)(1),
(2), (4) Date: May 21, 2014

(87) PCT Pub. No.: WO2012/172176
PCT Pub. Date: Dec. 20, 2012

(65) Prior Publication Data

US 2014/0249326 A1    Sep. 4, 2014

Related U.S. Application Data

(60) Provisional application No. 61/496,584, filed on Jun. 14, 2011.

(30) Foreign Application Priority Data

Jun. 14, 2011  (FI) ..................... 20115591

(51) Int. Cl.
| | | |
|---|---|---|
| C07F 7/18 | (2006.01) | |
| C07F 7/08 | (2006.01) | |
| C08G 77/04 | (2006.01) | |
| C08G 77/12 | (2006.01) | |
| C08G 77/14 | (2006.01) | |
| C08G 77/00 | (2006.01) | |

(52) U.S. Cl.
CPC ............ *C07F 7/188* (2013.01); *C07F 7/0859* (2013.01); *C07F 7/0874* (2013.01); *C07F 7/0896* (2013.01); *C07F 7/1808* (2013.01); *C07F 7/1892* (2013.01); *C08G 77/045* (2013.01); *C08G 77/12* (2013.01); *C08G 77/14* (2013.01); *C08G 77/80* (2013.01)

(58) Field of Classification Search
USPC ........................................ 556/450, 453, 457
See application file for complete search history.

(56) References Cited

U.S. PATENT DOCUMENTS 2,611,774 A   9/1952  Tyler
3,523,131 A * 8/1970  Sliwinski ............ C07F 7/0874
                                                556/453

5,883,214 A     3/1999  Wipfelder et al.
2011/0052890 A1  3/2011  Kim et al.

FOREIGN PATENT DOCUMENTS

| EP | 0725103 A2 | 1/1996 |
| EP | 1512724 A1 | 3/2005 |
| EP | 1852469 A1 | 11/2007 |
| GB | 1139423 | 2/1966 |
| JP | 8034854 A | 2/1996 |
| WO | WO 2005062080 A2 | 7/2005 |
| WO | WO 2009111190 A1 | 9/2009 |

OTHER PUBLICATIONS

Andrianov, K.A. et al: "Synthesis of 2,2-diorgano-1-OXA-2-silacyclohexanes and of [4-(acyloxy)butyl] cholorodiorganosilanes from the latter", Journal of General Chemistry USSR, Consultants Bureau, New York, NY, US, vol. 49, No. 5, Jan. 1, 1979.
Buttrus, Colin et al.: "Hydrogen bonding in organosilanediols. The crystal structure of di-i-propylsilanediol", Journal of Organometallic Chemistry, 302, p. 159-163, 1986.
Database Caplus [Online] Chemical Abstracts Service, Columbus, Ohio, US, 1979, XP002686015, retrieved from STN, Database accession No. 1979:187034.
Databse Caplus [Online] Chemical Abstracts Service, Columbus, Ohio, US, 1996, XP002686016, retrieved from STN, Database accession No. 1996:241840.
Database Caplus [Online] Chemical Abstracts Service, Columbus, Ohio, US, 2004, XP002686017, retrieved from STN, Database accession No. 2004:180028.
Database Caplus [Online] Chemical Abstracts Service, Columbus, Ohio, US, 2005, XP002686018, retrieved from STN, Database accession No. 2005:1345882.
Harris, Glyn: "A Study of Hydrogen Bonding in Poly(diorganosiloxane)", J. Chem. Soc., 5978, 1963.
Shimojima, Atsushi et al.: "Self-assembly of designed oligomeric siloxanes with alkyl chains into silica based hybrid mesostructures", J. Am. Chem. Soc., vol. 127, 2005.

* cited by examiner

*Primary Examiner* — Pancham Bakshi
(74) *Attorney, Agent, or Firm* — Seppo Laine Oy

(57) ABSTRACT

A method for preparation and polymerization of siloxane monomers of Formula I is presented. The synthesis includes the selective reaction between silanol containing unit and alkoxy containing units in the presence of basic catalyst. The siloxane monomers of the invention can be used for preparation of siloxane polymers with good flexibility and cracking threshold, and functional sites, useful for applications requiring low metal content in semiconductor industry.

1 Claim, 2 Drawing Sheets

METHOD OF SYNTHESIZING SILOXANE MONOMERS AND USE THEREOF

TECHNICAL FIELD

The present invention relates to polymers derived from siloxane monomers. In particular, the invention concerns a method of synthesizing siloxane monomers and of polymerizing monomers so obtained to produce siloxane polymers.

BACKGROUND ART

Flexible polysiloxane resins are useful spin-on dielectric and encapsulation materials. They are usually prepared by co-hydrolysis and subsequent condensation reaction between methyltrialkoxy-silane and other alkoxysilanes. They are used in semiconductor industry as insulation and planarising materials. Normally, they are spin-casted on a silicon wafer as polymer-solvent solutions, followed by soft bake at 100 to 150° C. to remove the solvent and final cure at 200 to 400° C., where remaining silanols thermally condense to form a cross-linked, insoluble film.

Methyltrialkoxysilane alone gives polymer with cracking threshold of only to 2 μm so, as such, it is unsuitable for thick films. A common co-monomer that is used to increase cracking threshold is diphenylsilanediol. However, compared to methyltrialkoxysilanes, diphenylsilanediol has low reactivity for which reason it is not easily co-polymerized into the polymer matrix. At normal hydrolysis conditions some of it remains non-reactive, and said monomer tends to crystallize out from the solution. If final spin-on solution contains unreacted diphenylsilanediol, some of it will fume out from the polymer film during the bake, causing a risk of particle contamination of process equipment.

There are some methods disclosed in the literature describing how to force diphenylsilanediol and other silanols of low reactivity to react into the polymer matrix. One way is to increase reaction temperature to over 100° C. with or without the use of catalysts such as aluminum, zirconium, tin or titanium catalysts (references 1 and 2). This, however, prevents the use of heat sensitive co-monomers in the polymer. Metal catalysts are difficult or even impossible to remove from the polymer solution. This severely limits the use of such polymers in semiconductor applications, where low metal contamination, often below 100 ppb total metals is required.

Another way of achieving forced incorporation of diphenylsilanediol into the polymer is to react it with chlorosilanes, such as methyltrichlorosilane, in the presence of an amine base as hydrogen chloride scavenger (reference 3). Unfortunately, chlorosilanes are very corrosive to laboratory and production equipment. Also the by-product, an amine-hydrochloride salt, needs to be removed from the reaction mixture by filtration, which is not readily achieved with moisture sensitive chlorosilanes.

One major problem in using diphenylsilanediol directly in materials for the semiconductor industry is that commercial grades of diphenylsilanediol contain metal impurities, sometimes even in the form of tiny rust particles. Being a solid material, it cannot be purified simply by distillation. This is a common problem with many silanol containing silane monomers with high or no boiling point combined with high melting points.

U.S. Pat. No. 3,122,579 discloses a method of preparing silane monomers in which an acetoxy- or chloro-modified monomer is reacted with silanol (Si—OH). The latter reaction causes a hydrochloro precipitate which is difficult to process, whereas the first reaction gives rise to acetoxysilanes which are difficult to hydrolyze because there is then formed acetic acid in equivalent amounts. For this reason, acetoxy silanes are rarely used for polymerization; they are primarily suitable for RTV-cured silicone materials as a cross-linking agent.

GB Patent Specification No. 1139423A discloses a method of preparing siloxanes by reacting hydridosilanes with hydroxysilanes in the presence of an amine catalyst. Hydridosilanes are expensive chemicals and in the reactions described in the document hydrogen, an explosive gas, is formed which causes a safety risk when operating the process on an industrial scale.

SUMMARY OF INVENTION

Technical Problem

It is an aim of the present invention to eliminate at least a part of the problems relating to the background art and to provide a method of producing monomers which can be used in the production of flexible polysiloxane resin.

Thus, the invention provides a new technical solution of producing silanol containing monomers while avoiding the problems of the art. Further, the present invention achieves a method of polymerizing silanol containing monomers with alkoxysilanes to give siloxane polymers with high selectivity and high yield.

Solution to Problem

It has surprisingly been found that silanol containing monomers, such as diphenylsilanediol, can be selectively reacted with alkoxysilanes in the presence of a basic catalyst, such as gaseous ammonia, to yield siloxane monomers with high selectivity and yield. The siloxane monomers thus obtained can be used for producing siloxane polymers by hydrolysis and condensation polymerization.

More specifically, the method according to the present invention is mainly characterized by what is stated in the characterizing part of claim 1.

The uses of the present invention are characterized by what is stated in claim 8.

Advantageous Effects of Invention

The present invention provides considerable advantages. Thus, during the reaction, no silanol-silanol self-condensation takes place. The present reaction gives no solid salts as byproduct. Isolation of the product is accomplished simply by distillation, which conveniently removes any metal contaminations which may be present in the silanol starting material. The obtained monomer can be then polymerized and hydrolyzed alone or with silane monomers, to yield polymeric siloxane resin material with high cracking threshold.

As shown below (cf. Example 3), the reaction can be carried out such that the grouping Si—H is protected and there will be a selective reaction between the alkoxy group and the hydroxyl silane.

BRIEF DESCRIPTION OF DRAWINGS

Next the invention will be examined more closely with the aid of a detailed description and with reference to the attached drawings, in which.

DESCRIPTION OF EMBODIMENTS

Figure 1:
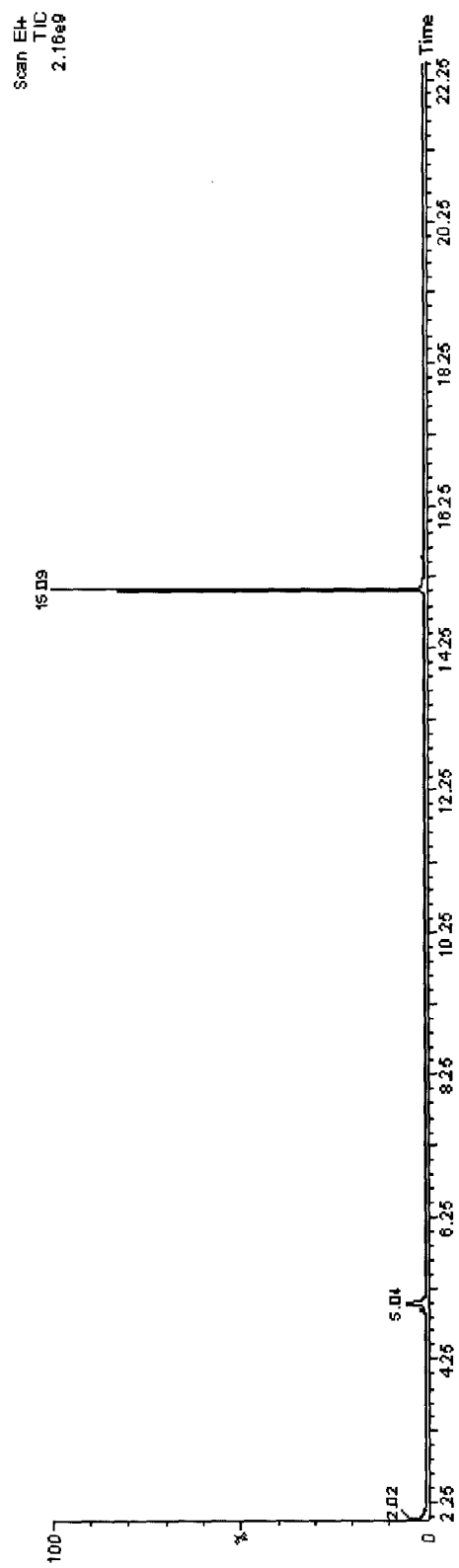
FIG. 1 shows the Gas Chromatogram (GC) of the reaction solution of Example 7.

As briefly discussed above, the present invention provides a method for the preparation of siloxane monomers of Formula I.

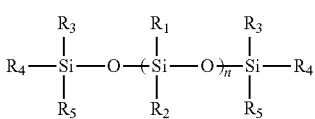

Formula I

In Formula I, n stands for an integer having a value in the range from 1 to 3;

$R_0$ is an unsubstituted or substituted, linear or branched alkyl, having 1 to 6 carbon atoms;

$R_1$ is an unsubstituted or substituted, linear or branched alkyl having 1 to 20 carbon atoms; an aryl group; an alkenyl group;

$R_2$ is an unsubstituted or substituted, linear or branched alkyl having 1 to 20 carbon atoms; an aryl group; an alkenyl group;

$R_3$, $R_4$ and $R_5$ independently stand for hydrogen or an unsubstituted or substituted, linear or branched alkyl having 1 to 20 carbon atoms; an aryl group; an alkenyl group; an alkoxy group having 1 to 4 carbon atoms.

In the above definitions, "alkyl" generally stands for a branched or linear, optionally substituted saturated hydrocarbyl radical (alkyl group).

In the meaning of $R_0$, the alkyl group stands for a lower alkyl containing 1 to 6 carbon atoms, which optionally bears 1 to 3 substituents selected from methyl and halogen. Particularly preferred examples of $R_0$ include methyl, ethyl, n- or i-propyl, and n-, t- or i-butyl.

Together with an adjacent oxygen atom, $R_0$ forms an alkoxy group, preferably a lower alkoxy group, such as methoxy, ethoxy or isopropoxy group, which optionally is substituted.

In the meaning of substituents $R_1$, $R_2$, $R_3$, $R_4$ and $R_5$, "alkyl" preferably stands for a hydrocarbyl radical having 1 to 18, more preferably 1 to 14 and particularly 1 to 12 carbon atoms. The alkyl can be linear or, when branched, preferably is branched at the alpha or beta position, optionally further substituted with one or more, preferably two, $C_1$ to $C_6$ alkyl groups, or halogenated, in particular partially or fully fluorinated or per-fluorinated. Examples include non-fluorinated, partially fluorinated and per-fluorinated i-propyl, t-butyl, but-2-yl, 2-methylbut-2-yl, and 1,2-dimethylbut-2-yl.

The aryl group is preferably phenyl, which optionally bears 1 to 5 substituents selected from halogen, alkyl or alkenyl on the ring, or naphthyl, which optionally bear 1 to 11 substituents selected from halogen alkyl or alkenyl on the ring structure, the substituents being optionally fluorinated (including per-fluorinated or partially fluorinated)

"Alkenyl" as used herein includes straight-chained and branched alkenyl groups, such as vinyl and allyl groups. Generally "alkenyl" contains 2 to 18, more preferably 2 to 14 and particularly preferred 2 to 12 carbon atoms. The ethylenic, i.e. two carbon atoms bonded with double bond, group is preferably located at the position 2 or higher, related to the Si atom in the molecule. Branched alkenyl is preferably branched at the alpha or beta position with one and more, preferably two, $C_1$ to $C_6$ alkyl, alkenyl or alkynyl groups, particularly preferred fluorinated or per-fluorinated alkyl, alkenyl or alkynyl groups.

The synthesis according to the present invention includes the selective reaction between silanol containing unit and alkoxy containing units in the presence of basic catalyst (cf. below reaction formula I).

Reaction scheme I

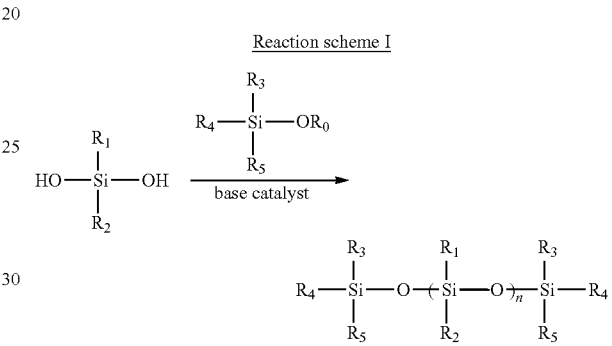

wherein symbols n and $R_0$, $R_1$, $R_2$, $R_3$, $R_4$ and $R_5$ have the same meaning as above in connection with Formula I.

The reaction is run at a temperature in the range from −78 to +60° C., depending on the reactivity of the components. If reaction is run at too low temperature, the rate of the reaction is too slow economically. If the reaction is run at too high temperature, side reactions such as alkoxylation or oligomerization of the silanol component, or other reactions, such as the reaction between Si—H and alcohol to form alkoxy group and hydrogen gas, may occur. The reaction time is from one minute to 100 hours. The progress of the reaction can be monitored by gas chromatography. If the reaction time is too short, low yields are obtained because unreacted starting silanol are still present. If the reaction time is too long, reactor throughput will suffer.

The silanol compound has the general formula II

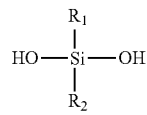

wherein symbols $R_1$ and $R_2$ have the same meaning as above in connection with Formula I.

Preferably the silanol compound is selected from the group comprising diethylsilanediol, dimethylsilanediol, dipropylsilanediol, diisopropylsilanediol, dibutylsilanediol, di-tert-butylsilanediol, di-iso-butylsilanediol, di-sec-butylsilanediol, diphenylsilanediol, dicyclohexylsilanediol, cyclohexylmethylsilanediol, cyclohexylethylsilanediol, 1,1,3,3-tetramethyldisiloxane-1,3-diol or 1,1,3,3-tetraphenyldisiloxane-1,3-diol, 1,1,3,3,5,5-hexaphenyltrisiloxane-1,5- diol, bis(p-yinylphenyl)silanediol, (p-vinylpheny) phenylsilanediol, phenylvinylsilanediol, or 1-adamantylsilanetriol.

The alkoxysilane of the reaction has the general formula III

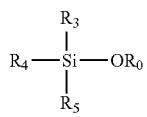

wherein symbols $R_3$, $R_4$ and $R_5$ have the same meaning as above in connection with Formula I.

Preferably the alkoxysilane compound is selected from the group comprising tetramethoxysilane, tetraethoxysilane, trimethoxysilane, triethoxysilane, methyltrimethoxysilane, methyltriethoxysilane, ethyltrimethoxysilane, ethyltriethoxysilane, propyltrimethoxysilane, propyltriethoxysilane, yinyltrimethoxysilane, vinyltriethoxysilane, vinylmethyldimethoxysilane, yinylmethyldiethoxysilane, vinyldimethylmethoxysilane, vinyldimethylethoxysilane, allyltrimethoxysilane, allyltriethoxysilane, allylmethyldimethoxysilane, allylmethyldiethoxysilane, allyldimethylmethoxysilane, allyldimethylethoxysilane, phenyltrimethoxysilane, phenyltriethoxysilane, diphenyldimethoxysilane, diphenyldiethoxysilane, metcaptopropyltrimethoxysilane, mercaptopropyltriethoxysilane, 3,3,3-trifluoropropyltrimethoxysilane, 3,3,3-trifluoropropyltriethoxysilane, 3,3,3-trifluoropropylmethyldimethoxysilane, 3,3,3-trifluoropropylmethyldiethoxysilane, 3-chloropropyltrimethoxysilane, 3-chloropropyltriethoxysilane, 3-chloropropylmethyldimethoxysilane, 3-chloropropylmethyldiethoxysilane, 3-chloropropyldimethylmethoxysilane, 3-chloropropyldimethylethoxysilane, chloromethyltrimethoxysilane, chloromethyltriethoxysilane, chloromethylmethyldimethoxysilane, chloromethylmethyldiethoxysilane, chloromethyldimethylmethoxysilane, chloromethyldimethylethoxysilane, dimethoxydimethylsilane, diethoxydimethylsilane, methoxydimethylsilane, ethoxydimethylsilane, methoxytrimethylsilane, ethoxytrimethylsilane, methylphenyldimethoxysilane, methylphenyldiethoxysilane, (p-yinylphenyl)trimethoxysilane, (p-vinylphenyl)triethoxysilane, (p-yinylphenyl)methyldimethoxysilane, (p-yinylphenyl)methyldiethoxysilane, 2-phenylethyltrimethoxysilane, 2-phenylethyltriethoxysilane.

The base catalyst is preferably selected from the group of ammonia and organic amines. In particular, the catalyst has a pKb value in the range of about 1.5 to 10, preferably about 2.0 to 8.

The catalyst is selected such that the reaction rate is optimized while side reactions are minimized. If the base catalyst is too weak, that is, it has pKb >10, the reaction becomes too sluggish. If the base catalyst is too strong, that is pKb <1.5, side reactions tend to take place. It is preferred, that the catalyst has sufficient volatility, so it can be easily stripped out after the reaction. Alternatively, it may be also neutralized by using stoichiometric amount of acid such as but not limited to acetic acid, formic acid or hydrogen chloride. However, using too much acid may cause redistribution (=scrambling) of siloxane bonds and thus lower the yield.

The basic catalyst is selected from ammonia, pyridine, picoline, ethanolamine, methylamine, dimethylamine, trimethylamine, ethylamine, diethylamine, triethylamine, isopropylamine, diisopropylamine, diisopropylethylamine, propylamine butylamine sec-butylamine.

It is preferred to carry out the reaction according to reaction scheme I in a solvent. It is particularly preferred to select a solvent having a melting point which is so low that the solvent remains liquid at the low temperatures used during the synthesis. On the other hand, the boiling point of the solvent is preferably low enough so that it can be easily removed from the product by distillation. It is desirable that the silanol compound is soluble or essentially soluble in the solvent.

The solvent should preferably not react with the compounds used in the reaction.

Based on the above criteria, the solvent is selected from the group of cyclic or linear or branched ethers, such as tetrahydrofuran, 2-methyltetrahydrofuran, diethyl ether, diisopropyl ether, dibutyl ether, 1,2-dimethoxyethane, 1,2-dimethoxypropane, 1,2-diethoxyethane, 1,2-diethoxypropane, methyl t-butyl ether, ethyl t-butyl ether, or from the group of aliphatic hydrocarbons, such as pentane, hexane, heptane, and octane, or from the group of polar solvents, such as n-methylpyrrolidone, dimethylsulfone, dimethylformamide, diethylformamide, dimethylacetamide, tetramethylurea and dimethylsulfoxide, n-methylpyrrolidone and dimethylsulfone being particularly preferred. The solvent can also be a mixture of solvents, preferably a mixture of the listed solvents.

Although the reaction may be run also completely without solvent, that may cause problems with proper agitation and may lower the reaction rate.

The molar ratio of the silanol containing silane and the alkoxysilane is selected so that alkoxysilane is present at least equivalent amount to silanols, preferably in an excess of 2 to 5 times the molar amount of the silanol containing silane. If the ratio of alkoxysilane to silanol is below 1, low yields result from oligomerization of the reactants. If the ratio is above 5, the reaction becomes uneconomical.

The mass ratio of the solvent to the silanol silane is preferably 0.1 to 5. If the ratio is too low, problems with agitation may arise due to high amount of insoluble components in the reaction solution. If the ratio is above 5, the reaction becomes uneconomical.

The mass ratio of the base catalyst to silanol silane is preferably 0.001 to 1. If the ratio is too low, acidic impurities of the reaction components may complete neutralize the base, resulting in total suppression of the reactivity. If the ratio is above 1, the removal of the base may become difficult, and the reaction becomes uneconomical.

Of the monomers according to Formula I several are novel. Thus, the present invention covers novel monomers of Formula I

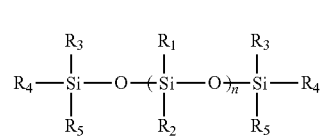

Formula I wherein
n stands for an integer having a value in the range from 1 to 3;
$R_0$ is an unsubstituted or substituted, linear or branched alkyl, having 1 to 6 carbon atoms;

$R_1$ is an unsubstituted or substituted, linear or branched alkyl having 1 to 20 carbon atoms; an aryl group; an alkenyl group;

$R_2$ is an unsubstituted or substituted, linear or branched alkyl having 1 to 20 carbon atoms; an aryl group; an alkenyl group;

$R_3$, $R_4$ and $R_5$ independently stand for hydrogen or an unsubstituted or substituted, linear or branched alkyl having 1 to 20 carbon atoms; an aryl group; an alkenyl group; or an alkoxy group having to 4 carbon atoms, excluding a compound according to formula wherein n=1, $R_3$ stands for methoxy, $R_4$ and $R_5$ stands for hydrogen and $R_1$ and $R_2$ both stand for phenyl, and further excluding a compound according to formula wherein n=1, $R_3$ and $R_4$ stand for methoxy, $R_5$ stands for hydrogen and $R_1$ and $R_2$ both stand for phenyl.

In particular, the monomers selected from the following group:

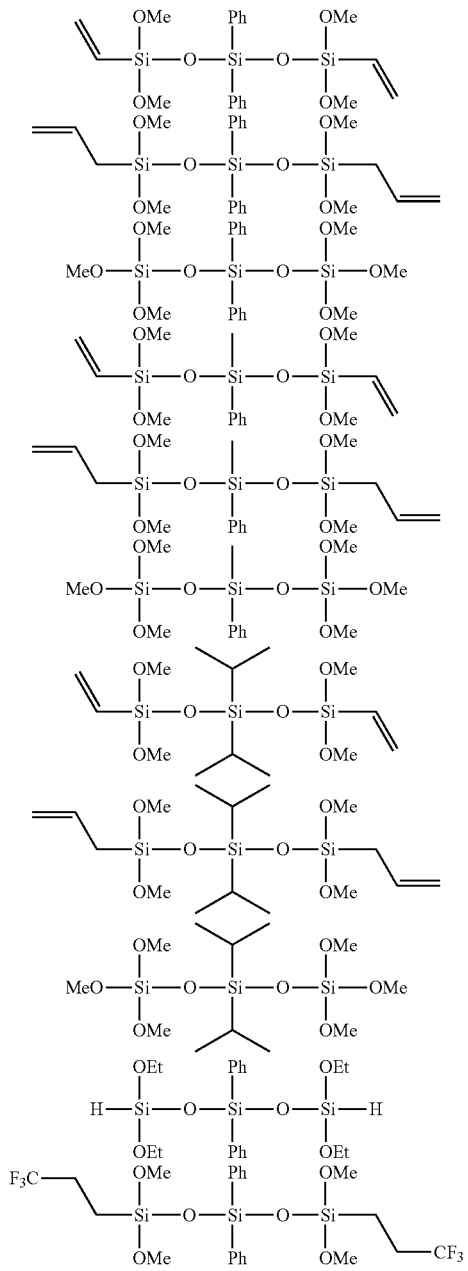

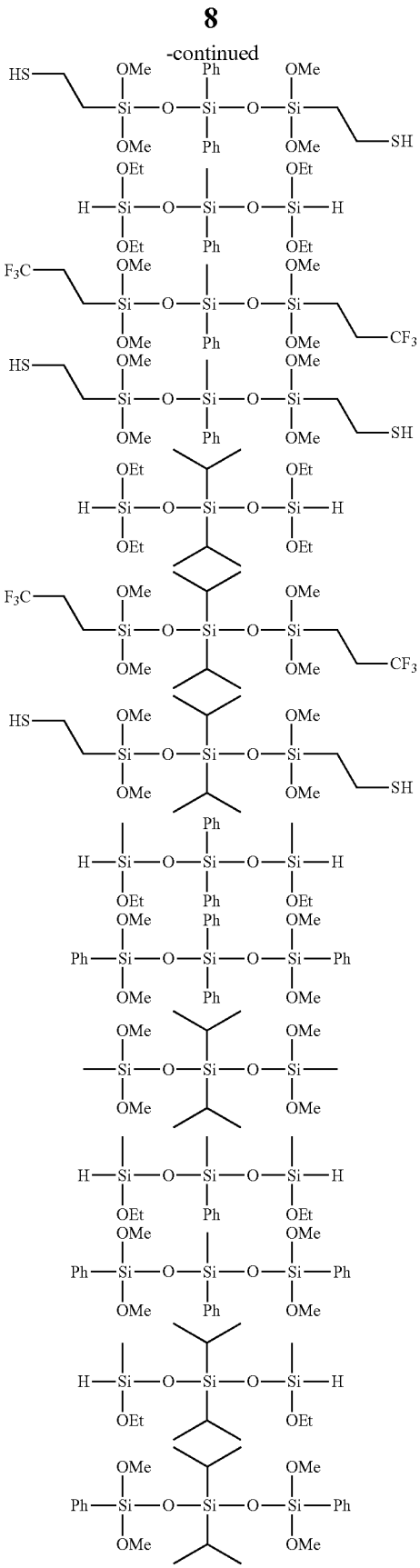

The monomers obtained according to Reaction scheme I are useful in the preparation of siloxane polymers with good flexibility and cracking threshold, and functional sites, useful for applications requiring low metal content in semiconductor industry.

Such siloxane polymers typically have a mass average molecular weight in the range from 500 to 1,000,000 g/mol, in particular 750 to 500,000 g/mol, for example about 800 to 100,000 g/mol.

Thus, the monomers obtained can be hydrolyzed polymerized with water and acid or base catalyst with or without co-monomers. The monomer of the invention is present in the monomer mixture at least 10 mol percent, preferably about 15 to 95 mol percent.

The monomers of the invention that contain vinyl, allyl or Si—H groups can also be polymerized by hydrosilylation reaction using platinum or palladium catalysts.

The other monomer(s) of the monomer mixture are typically other alkoxysilanes, such as tetra- or trialkoxysilanes, wherein the alkoxy groups have the same meaning as defined above for the alkoxy silane of Formula III. Thus, the comonomer(s) can be selected from the group of tetramethoxysilane, tetraethoxysilane trimethoxysilane, triethoxysilane, methyltrimethoxysilane, methyltriethoxysilane, ethyltrimethoxysilane, ethyltriethoxysilane, propyltrimethoxysilane, propyltriethoxysilane, vinyltrimethoxysilane, vinyltriethoxysilane, vinylmethyldimethoxysilane, vinylmethyldiethoxysilane, vinyldimethylmethoxysilane, vinyldimethylethoxysilane, allyltrimethoxysilane, allyltriethoxysilane, allylmethyldimethoxysilane allylmethyldiethoxysilane, allyldimethylmethoxysilane, allyldimethylethoxysilane, phenyltrimethoxysilane, phenyltriethoxysilane, diphenyldimethoxysilane, diphenyldiethoxysilane, metcaptopropyltrimethoxysilane, mercaptopropyltriethoxysilane, trifluoropropyltrimethoxysilane, 3,3,3-trifluoropropyltriethoxysilane, 3,3,3-trifluoropropylmethyldimethoxysilane, 3,3,3-trifluoropropylmethyldiethoxysilane, 3-chloropropyltrimethoxysilane, 3-chloropropyltriethoxysilane, 3-chloropropylmethyldimethoxysilane, 3-chloropropylmethyldiethoxysilane, 3-chloropropyldimethylmethoxysilane, 3-chloropropyldimethylethoxysilane, chloromethyltrimethoxysilane, chloromethyltriethoxysilane, chloromethylmethyldimethoxysilane, chloromethylmethyldiethoxysilane, chloromethyldimethylmethoxysilane, chloromethyldimethylethoxysilane, dimethoxydimethylsilane, diethoxydimethylsilane, methoxydimethylsilane, ethoxydimethylsilane, methoxytrimethylsilane, ethoxytrimethylsilane, methylphenyldimethoxysilane, methylphenyldiethoxysilane, (p-vinylphenyl)trimethoxysilane, (p-vinylphenyl)triethoxysilane, (p-vinylphenyl)methyldimethoxysilane, (p-vinylphenyl)methyldiethoxysilane, 2-phenylethyltrimethoxysilane, 2-phenylethyltriethoxysilane.

In the polymerization reaction, the acid catalyst can be selected from the group consisting of hydrochloric acid, nitric acid, trifluoroacetic acid, acetic acid, formic acid, oxalic acid, maleic acid, citric acid, phosphoric acid.

In the polymerization reaction, the base catalyst can be selected from the group consisting of ammonia, trimethylammonium hydroxide, triethylammonium hydroxide, tripropylammonium hydroxide, tributylammonium hydroxide.

The polymerization reaction can be carried out in a solvent selected, for example, from the group consisting of acetone, ethyl methyl ketone, tetrahydrofuran methanol, ethanol propanol, 2-propanol, butanol, 2-butanol, tort-butanol, 2-methyl-2-butanol, methyl acetate, ethyl acetate, propyl acetate, butyl acetate, propylene glycol methyl ether (PGME), propylene glycol ethyl ether (PGEE), propylene glycol propyl ether (PnP), propylene glycol methyl ether acetate (PGMEA), 1,2-dimethoxyethane, 1,2-dimethoxypropane.

Based on the above, in one embodiment, the hydrolysis polymerization is accomplished by adding water 1 to 5 equivalents, usually as 0.001 to 0.1M acid solution. The acid is selected from hydrochloric acid, nitric acid, trifluoroacetic acid, acetic acid, formic acid, oxalic acid, maleic acid, citric acid and phosphoric acid. The polymerization is carried out for 1 to 24 hours at 0 to 150° C.

If the polymerization time is too short and reaction temperature too low, incomplete hydrolysis may result in low molecular weight of the polymer. Unreacted alkoxy groups may remain in the polymer. If the polymerization time is too long and/or reaction time is too high, gelling of the polymer may take place.

If the polymer has too low molecular weight, it can be further heated at 100 to 200° C. in a solvent with or without a basic catalyst, such as triethylamine. Duration of the heating is decided by taking samples from the solution for GPC. When the target molecular weight is obtained, the reaction is cooled down and amine catalyst neutralized by washing with dilute acid, followed by DI-water.

The composition obtained by the above procedure typically can be formulated into a siloxane polymer composition containing a siloxane polymer, as described above, along with a solvent and additives.

Due to the particular manufacturing process of the monomer, any siloxane polymer composition obtained as disclosed will have a low metal content; in particular it has been found that the metal impurity may be as low as below 100 ppb.

The following non-limiting examples illustrate the invention.

EXAMPLES

Example 1

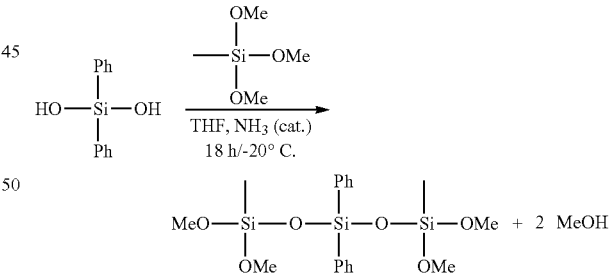

Diphenylsilanediol (60 g), tetrahydrofuran (THF, 30 g) and methyltrimethoxysilane (MTMOS, 180 g) were placed in a 500 mL 3-neck round bottom flask with a stir bar and reflux condenser. The flask was cooled to −20° C. Ammonia gas (~8 g) was slowly bubbled into the solution while stirring, until the solution became clear. The reaction was allowed to proceed for 18 hours at −20° C. It was then heated up to 70° C. and refluxed for one hour to remove ammonia. A distillation condenser was then attached to the flask, and vacuum was slowly applied to remove methanol, THF, and excess MTMOS. The remaining liquid was distilled at 150 . . . 160° C./0.1 mbar to give 1,1,5,5-tetramethoxy- 1,5-dimethyl-3,3-diphenyltrisiloxane as colorless liquid (97 g, 82%, purity >99% by GC/MS).

Example 2

Diphenylsilanediol (60 g), tetrahydrofuran (THF, 50 g) and phenyltrimethoxysilane (PhTMOS, 300 g) were placed in a 500 mL 3-neck round bottom flask with a stir bar and reflux condenser. The flask was cooled to −20° C. Ammonia gas (~8 g) was slowly bubbled into the solution while stirring until the solution became clear. The reaction was allowed to proceed for 18 hours at −20° C. It was then heated up to 70° C. and refluxed for one hour to remove ammonia. A distillation condenser was then attached to the flask, and vacuum was slowly applied to remove methanol and THF. The remaining liquid was distilled at 120° C./0.1 mbar to remove excess PhTMOS, followed by the distillation at 210 . . . 230° C./0.1 mbar to give 1,1,5,5-tetramethoxy-1,3,3,5-tetraphenyltrisiloxane as colorless, viscous liquid (117 g, 77%).

Example 3

Diphenylsilanediol (60 g), tetrahydrofuran (THF, 30 g) and triethoxysilane (HTEOS, 185 g) were placed in a 500 mL 3-neck round bottom flask with a stir bar and reflux condenser. The flask was cooled to −10° C. Pyridine (~3 g) was added into the solution. The reaction was allowed to proceed for 18 hours at −10° C. A distillation condenser was then attached to the flask, and vacuum was slowly applied to remove ethanol, THF, pyridine, and excess HTEOS. The remaining liquid was distilled at 140 . . . 170° C./0.1 mbar to give 1,1,5,5-tetraethoxy-3,3-diphenyltrisiloxane as colorless liquid (105 g, 84%).

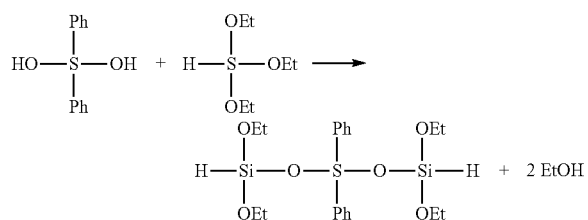

Thus, in the reaction, the grouping Si—H is protected and there is a selective reaction between the alkoxy group and the hydroxyl silane.

Example 4

Diphenylsilanediol (60 g), tetrahydrofuran (THF, 30 g) and vinyltrimethoxysilane (VTMOS, 200 g) were placed in a 500 mL 3-neck round bottom flask with a stir bar and reflux condenser. The flask was cooled to −20° C. Ammonia gas (~8 g) was slowly bubbled into the solution while stirring until the solution became clear. The reaction was allowed to proceed for 18 hours at −20° C. It was then heated up to 70° C. and refluxed for one hour to remove ammonia. A distillation condenser was then attached to the flask, and vacuum was slowly applied to remove methanol, THF, and excess VTMOS. The remaining liquid was distilled at 150 . . . 170° C./0.1 mbar to give 1,1,5,5-tetramethoxy-1,5-divinyl-3,3-diphenyltrisiloxane as colorless liquid (104.5 g, 87%).

Example 5

Diisopropylsilanediol (10 g, prepared by known methods, cf. reference 4), tetrahydrofuran (THF, 5 g) and methyltrimethoxysilane (MTMOS, 60 g) were placed in a 250 mL 3-neck round bottom flask with a stir bar and a reflux condenser. The flask was cooled to −20° C. Ammonia gas (~3 g) was slowly bubbled into the solution while stirring until the solution became clear. The reaction was allowed to proceed for 18 hours at −20° C. It was then heated up to 70° C. and refluxed for one hour to remove ammonia. A distillation condenser was then attached to the flask, and vacuum was slowly applied to remove methanol, THF, and excess MTMOS. The remaining liquid was distilled at 130 . . . 150° C./0.1 mbar to give 1,1,5,5-tetramethoxy-1,5-dimethyl-3,3-diisopropyltrisiloxane as colorless liquid (18 g, 75%).

Example 6

Diphenylsilanediol (60 g), tetrahydrofuran (THF, 30 g) and tetramethoxysilane (TMOS, 200 g) were placed in a 500 mL 3-neck round bottom flask with a stir bar and reflux condenser. The flask was cooled to −20° C. Ammonia gas (~8 g) was slowly bubbled into the solution while stirring until the solution became clear. The reaction was allowed to proceed for 18 hours at −20° C. It was then heated up to 70° C. and refluxed for one hour to remove ammonia. A distillation condenser was then attached to the flask, and vacuum was slowly applied to remove methanol, THF, and excess TMOS. The remaining liquid was distilled at 150 . . . 170° C./0.1 mbar to give 1,1,1,5,5,5-hexamethoxy-3,3-diphenyltrisiloxane as colorless liquid (115 g, 90%).

Example 7

Figure 2:
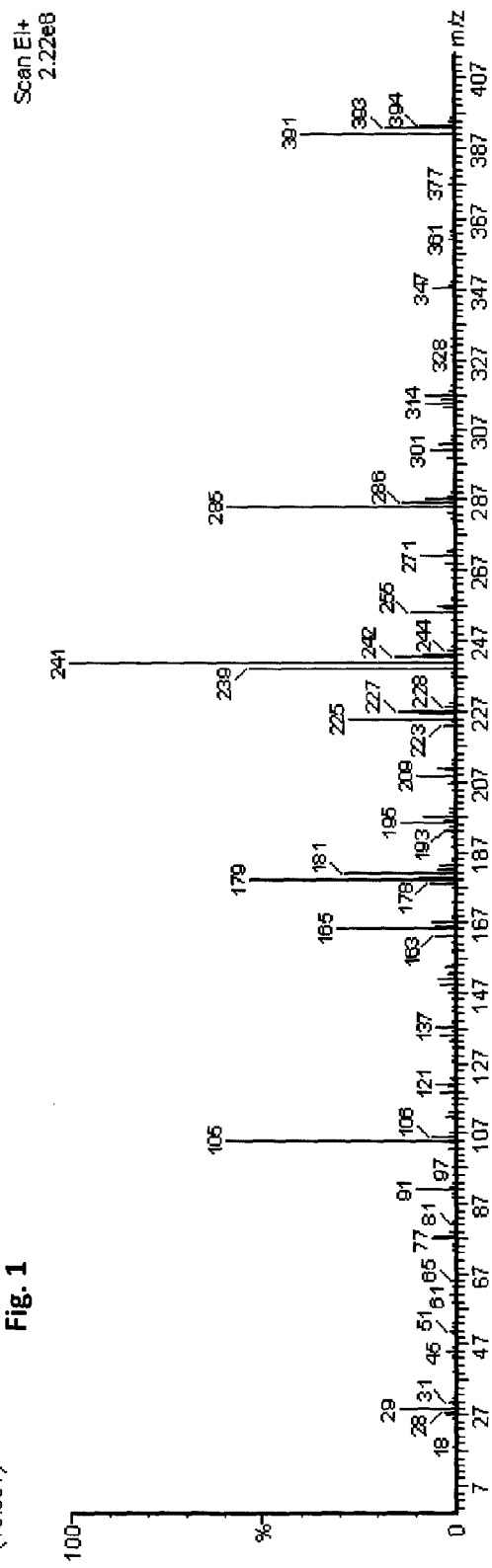
FIG. 2 shows the Mass Spectrum of the peak from the reaction solution of Example 7 at 15 minutes.

Diphenylsilanediol (5 g), tetrahydrofuran (THF, 4 g) and methyldiethoxysilane (MHDEOS, 15 g) were placed in a 50 mL 3-neck round bottom flask with a stir bar and reflux condenser. The flask was kept at +23° C., while ethanolamine (0.1 mL) was added. The reaction was allowed to proceed for 10 minutes at 23 . . . 40° C., after which GC/MS was run. The high-boiling components of the reaction solution were shown to contain exclusively 1,5-dimethyl-1,5-diethoxy-3,3-diphenyltrisiloxane (FIGS. 1 and 2).

Example 8

Diphenylsilanediol (5 g), tetrahydrofuran (THF, 4 g) and mercaptopropyltrimethoxysilane (MPTS, 30 g) were placed in a 100 mL 3-neck round bottom flask with a stir bar and reflux condenser. The flask was kept at +0° C., while ammonia (~1 g) was bubbled in. The reaction was allowed to proceed for 4 hours at 0° C., followed by 18 hours warming to room temperature. When GC/MS was run, a peak corresponding to 1,5-bis(mercaptopropyl)-1,1,5,5-tetramethoxy-3,3-diphenyltrisiloxane was seen, along with unreacted excess MPTS.

Example 9

Phenylmethylsilanediol (4 g), tetrahydrofuran (THF, 4 g) and VTMOS (20 g) were placed in a 50 mL 3-neck round bottom flask with a stir bar and reflux condenser. The flask was kept at −15° C., while ammonia (~1 g) was bubbled in. The reaction was allowed to proceed for 2 hours at 45° C., followed by 18 hours at −20° C. When GC/MS was run, a single peak, corresponding to 1,5-divinyl-1,1,5,5-tetramethoxy-3-phenyl-3-methyltrisiloxane was seen, along with unreacted excess VTMOS.

Example 10

Cyclohexylmethylsilanediol (4 g), tetrahydrofuran (THF, 4 g) and VTMOS (20 g) were placed in a 50 mL 3-neck round bottom flask with a stir bar and reflux condenser. The flask was kept at −15° C., while ammonia (~1 g) was bubbled in. The reaction was allowed to proceed for 1 hour at −15° C. followed by 18 hours at −20° C. When GC/MS was run, a single peak, corresponding to 1,5-divinyl-1,1,5,5-tetramethoxy-3-cyclohexyl-3-methyltrisiloxane was seen, along with unreacted excess VTMOS.

Example 11

1,1,3,3-Tetramethyldisiloxane-1,3-diol (4 g, prepared by a known method, cf. reference 5), tetrahydrofuran (THF, 10 g) and VTMOS (30 g) were placed in a 100 mL 3-neck round bottom flask with a stir bar and reflux condenser and cooled to −20° C. Ammonia (~1 g) was bubbled in. The reaction was allowed to proceed for 18 hour at −20° C. The solution was stripped from low boiling material in a rotary evaporator, followed by short path distillation at 100 . . . 135° C./<5 mbar. GC/MS of the distillate (8 g) showed only two peaks, corresponding to 1,1,7,7-tetramethoxy-1,7-divinyl-3,3,5,5-tetramethyltetrasiloxane (73.1%) and 1,1,5,5-tetramethoxy-3,3-dimethyltrisiloxane (25.9%). This equals to 88.6% overall yield, based on tetramethyldisiloxanediol.

Example 12

1,1,3,3-Tetramethyldisiloxane-1,3-diol (2.4 g), tetrahydrofuran (THF, 5 g) and HTEOS (16 g) were placed in a 50 mL 3-neck round bottom flask with a stir bar and reflux condenser and cooled to −25° C. Three drops of pyridine were added. The reaction was allowed to proceed at −25° C. No hydrogen evolution was seen during the reaction. After six hours, low boiling volatiles were removed in a rotary evaporator, and the remaining liquid was vacuum distilled at 60 . . . 80° C./<1 mbar. GC/MS was run of the distillate (5.1 g), and only two peaks were seen, corresponding to 1,1,77-tetraethoxy-3,3,5,5-tetramethyltetrasiloxane (73.0%) and 1,1,5,5-tetraethoxy-3,3-dimethyltrisiloxane (27.0%). This equals to 93.1% overall yield, based on tetramethyldisiloxanediol.

Example 13

Figure 3:
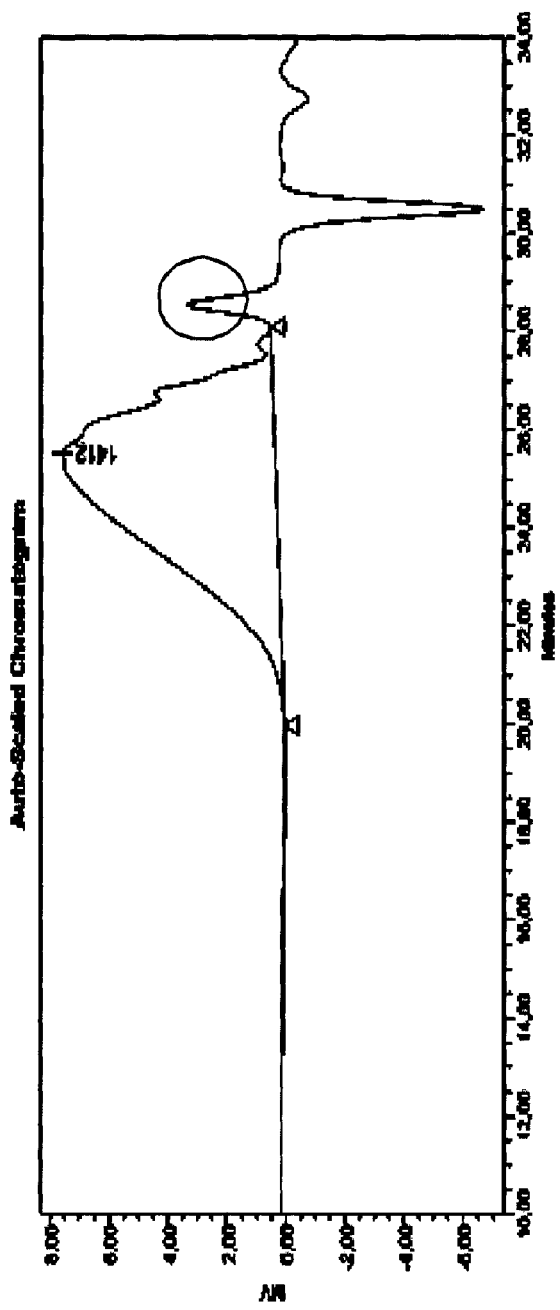
FIG. 3 shows the Gel Permeation Chromatogram (GPC) curve of the polymer from Example 13, only low amount of diphenylsilanediol being seen at 28.5 minutes.

Glycidyloxypropyltrimethoxysilane (13.3 g) and monomer from Example 1 (31.8 g) were placed in a 250 mL rb flask, along with acetone (55 g). Dilute HCl (22 g, 0.01M) was then added, and the hydrolysis condensation reaction was allowed to proceed at reflux for five hours. After the reflux, the solution was visually clear. It was taken to rotary evaporator and PGMEA( ) was added. Evaporation was continued until solid content of the polymer solution was 40%. After adding 5% DIW, the solution was further heated at 100° C. for 2 hours. GPC showed low amount of oligomers (FIG. 3, circled). Mw=3,500 g/mol. The material was photo patternable by UV@365 nm when 2% Rhodorsil® 2074 (an iodonium borate salt by Rhodia Inc.) and 0.5% Anthracure® UVS-1221 (9,10-dipropoxyanthracene by Kawasaki Kasei Chemicals Ltd.) were added as photoacid and sensitizer. Over 17 μm thick films were prepared which did not crack. The film did not fume during the soft bake at 150° C./5 min or cure at 200° C./30 min.

Polymer of Example 13.

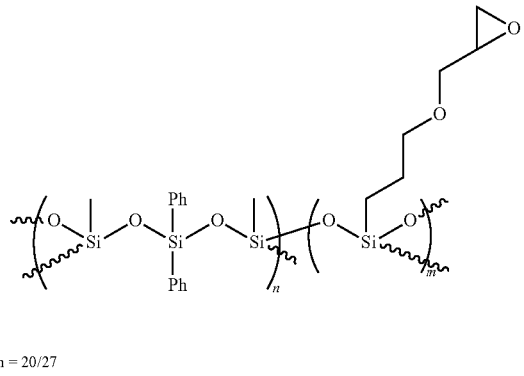

m/n = 20/27

Example 14

1,1,5,5-Tetraethoxy-3,3-diphenyltrisiloxane (5 g) from example 3 and 1,4-cyclohexyldimethanol divinyl ether (3.25 g) were placed in a 30 mL clean glass vial. Karsted's catalyst was injected (10 μL as 2% xylene solution), and the hydrosilylation reaction was allowed to proceed for 24 hours, after which no remaining vinyl peak was seen by FTIR. Mw/Mn=4,962/1,753 was measured by GPC. The polymer was diluted by acetone (25 g), and nitric acid (0.01M, 2.5 ekv) was added to hydrolyze ethoxy groups of the polymer. The reaction was again allowed to proceed for 24 h at +23° C. after which the solvents were exchanged to PGMEA by rotary evaporator. Polymer with Mw/Mn=11,512/2,211 was obtained. The material was spin-casted as a 16% solution containing PGMEA/MEK (60/40) and 1% BYK®-306 (surfactant by BYK-Chemie GmbH). The film was soft baked at 130° C./1 min, followed by cure at 200° C./60 min. An elastic and scratch resistant clear film (Tx=575 nm, RI=1.55, Shrinkage 1.8%) was obtained.

Polymer of Example 14.

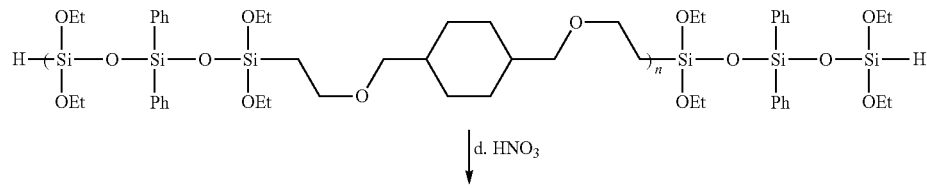

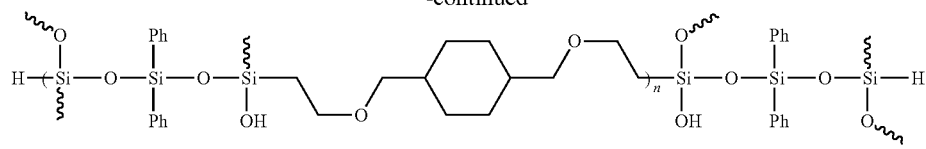

Comparative Example 1

Diphenylsilanediol (60 g), tetrahydrofuran (THF, 30 g) and triethoxysilane (HTEOS, 180 g) were placed in a 500 mL 3-neck round bottom flask with a stir bar and reflux condenser. The reaction was allowed to proceed in the absence of ammonia catalyst for 24 hours at +23° C. GC/MS showed that no desired reaction had taken place. Only some alkoxy/OH exchange between silanediol and HTEOS had occurred, to give ethoxydiphenylsilanol and diethoxydiphenylsilane.

Comparative Example 2

Diphenylsilanediol (60 g), tetrahydrofuran (THF, 30 g) and methyltrimethoxysilane (MTMOS, 180 g) were placed in a 500 mL 3-neck round bottom flask with a stir bar and reflux condenser. The reaction was allowed to proceed without ammonia catalyst for 24 hours at +23° C. GC/MS showed that no desired reaction had taken place. Only some alkoxy/OH exchange between silanediol and MTMOS had occurred, to give methoxydiphenylsilanol and dimethoxydiphenylsilane.

Comparative Example 3

Diphenylsilanediol (60 g), tetrahydrofuran (THF, 30 g) and methyltrimethoxysilane (MTMOS, 180 g) were placed in a 500 mL 3-neck round bottom flask with a stir bar and reflux condenser. The flask was cooled to −20° C. 1,8-Diazabicycloundec-7-ene (DBU, 0.5 g) was added into the solution. The reaction was allowed to proceed for 5 hours at −20° C., after which GC/MS was run from the reaction mixture. It showed, that while low yields of the desired product was formed, over 80% of diphenylsilanediol was converted to dimethoxydiphenylsilane. DBU (pKb=1.1) was clearly too strong base for this reaction and caused excessive side reactions.

Comparative Example 4

Figure 4:
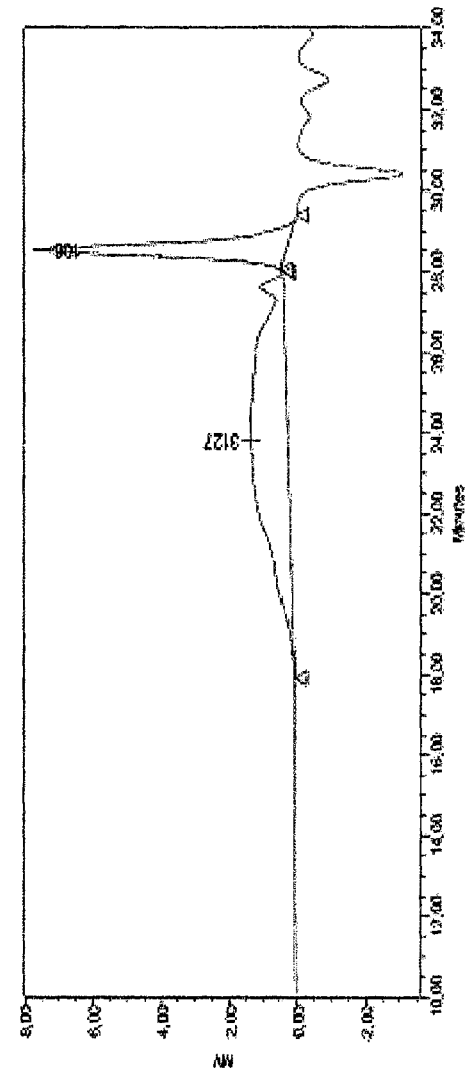
FIG. 4 shows the Gel Permeation Chromatogram (GPC) curve of the polymer from Comparative Example 3; peak corresponding to high amount of unreacted diphenylsilanediol is seen at 28.5 minutes.

Glycidyloxypropyltrimethoxysilane (13.3 g) and diphenylsilanediol (16.2 g), and MTMOS (20.5 g) were placed in a 250 mL rb flask, along with acetone (50 g). Dilute HCl (17 g, 0.01M) was then added, and the hydrolysis condensation reaction was allowed to proceed at reflux for five hours. After the reflux, the solution was visually cloudy, and contained white and brown particles. The white particles were likely unreacted diphenylsilanediol, while brown particles were rust that was contamination in the commercial diphenylsilanediol. The polymer was taken to a rotary evaporator and PGMEA (3×100 g) was added. Evaporation was continued until the solid content of the solution was 40%. After adding 5% DIW, the solution was heated at 100° C. for two hours. GPC showed high amount of unreacted diphenylsilanediol (FIG. 4). The material was photo patternable, when 2% Rhodorsil® 2074 (an iodonium borate salt by Rhodia Inc.) and 0.5% Anthracure® UVS-1221 (9,10-dipropoxyanthracene by Kawasaki Kasei Chemicals Ltd.) were added as photoacid and sensitizer. During the softbake at 150° C. and cure at 200° C., the material was fuming strongly. Thick films >10 μm cracked.

INDUSTRIAL APPLICABILITY

The present siloxane monomers of the invention are useful for the preparation of siloxane polymers with good flexibility and cracking threshold, and functional sites, useful for applications requiring low metal content in semiconductor industry. In particular the siloxane polymer can be used for dielectric applications in the semiconductor industry.

CITATION LIST

1. U.S. Pat. No. 5,883,214
2. US 20110052890
3. EP 0725103A2
4. Buttrus, Nabeel H. et al., *J. Organomet. Chem.* 1986, 302(2), 159–63
5. Harris, G. L, *J. chem. Soc.* 1963, 5978

The invention claimed is:
1. A monomer of the following formula

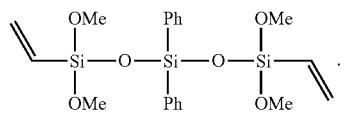 [SMILES: C=C[Si](OC)(OC)O[Si](O[Si](C=C)(OC)OC)(c1ccccc1)c1ccccc1]

* * * * *